United States Patent [19]

Denen et al.

[11] Patent Number: 5,352,868
[45] Date of Patent: Oct. 4, 1994

[54] RESISTANCE FEEDBACK CONTROLLED POWER SUPPLY

[75] Inventors: Dennis J. Denen, Columbus; John J. Knittle, Westerville; Albert E. Weller, III, Columbus, all of Ohio

[73] Assignee: Hemostatic Surgery Corporation, Georgetown, Ky.X

[21] Appl. No.: 877,699

[22] Filed: May 1, 1992

[51] Int. Cl.$^5$ .............................................. H05B 1/02
[52] U.S. Cl. ...................... 219/501; 219/497; 219/505; 219/499; 307/125
[58] Field of Search ............. 219/491, 494, 497, 499, 219/501, 505, 507–509; 307/117, 125

[56] References Cited

U.S. PATENT DOCUMENTS

| | | | |
|---|---|---|---|
| 4,523,084 | 6/1985 | Tamura et al. | 219/497 |
| 4,549,073 | 10/1985 | Tamura et al. | 219/497 |
| 4,590,934 | 5/1986 | Malis et al. | 128/303.14 |
| 4,626,767 | 12/1986 | Clappier et al. | 323/280 |
| 4,662,369 | 5/1987 | Ensslin | 128/303.13 |
| 4,736,091 | 4/1988 | Moe | 219/505 |
| 4,744,359 | 5/1988 | Hatta et al. | 219/497 |
| 4,752,864 | 6/1988 | Clappier | 363/86 |
| 4,778,980 | 10/1988 | Rathbun | 219/501 |
| 4,795,886 | 1/1989 | Carter, Jr. | 219/505 |
| 4,903,696 | 2/1990 | Stasz et al. | 606/37 |
| 4,938,761 | 7/1990 | Ensslin | 606/31 |
| 4,961,739 | 10/1990 | Thompson | 606/37 |
| 4,969,885 | 11/1990 | Farin | 606/38 |
| 5,128,602 | 7/1992 | Carter, Jr. | 323/267 |

FOREIGN PATENT DOCUMENTS

| | | |
|---|---|---|
| 3531576 | 5/1986 | Fed. Rep. of Germany . |
| 51-15160 | 4/1976 | Japan . |
| 53-28399 | 8/1976 | Japan . |

*Primary Examiner*—Mark H. Paschall
*Attorney, Agent, or Firm*—Nicola A. Pisano

[57] ABSTRACT

A power supply for use with resistively-heated surgical instruments is provided, wherein accurate temperature regulation is achieved employing a resistance feedback circuit. The power supply powers the surgical instrument with an AC voltage waveform, and applies a fixed, low level DC signal to the heating element to produce a DC signal proportional to the instantaneous resistance of the heating element. The DC signal is compared to a setpoint value to obtain a control signal for adjusting the power delivered to the instrument to maintain a substantially constant heating element temperature, even under varying thermal loads.

19 Claims, 3 Drawing Sheets

RESISTANCE FEEDBACK CONTROLLED POWER SUPPLY

This invention relates to power supplies for use with surgical instruments, more particularly, to power supplies for use with resistively-heated hemostatic surgical instruments.

BACKGROUND OF THE INVENTION

Hemostatic surgical techniques, in which heated instruments are used to thermally reform the collagen of incised tissue during surgery, are well known. For example, heated scalpel blades have been used that prevent bleeding by causing hemostasis of tissue as it is cut. It is frequently desirable to operate such surgical instruments at a selected operating temperature, depending upon the type of surgery to be performed.

Typically, resistively-heated surgical instruments are powered by an adjustable power supply to achieve a desired operating temperature. The operating temperature of the blade is generally adjusted by selecting an appropriate power level on the power supply. However, with previously known power supplies, it is often difficult to maintain a constant blade temperature, as the thermal load placed on the instrument causes the blade temperature to fluctuate considerably during a surgical procedure.

For example, as the blade of the surgical instrument passes through fresh tissue, the temperature of the blade may drop, thus requiring the power supply to increase the power supplied to the surgical instrument to maintain the selected operating temperature. As the temperature of the surgical instrument fluctuates, the thermal energy deposited by the surgical instrument in the adjacent tissue therefore also varies, and may result in uneven or ineffective hemostasis.

It would therefore be desirable to provide a power supply that enables an operator to select a desired instrument operating temperature, and that monitors the instrument temperature and adjusts the power that is delivered to the instrument to maintain a substantially constant instrument operating temperature under varying thermal loads.

It is known that the application of electrical power to a resistively-heated surgical instrument may result in current leakage to the patient. Where the current is supplied in the form of a direct current voltage waveform, or an alternating-current waveform having a frequency of less than about 100 kHz, undesirable neuromuscular stimulation of the patient may occur. Such stimulation may interfere with the surgeon's ability to manipulate the surgical instrument, and may also injure the patient. On the other hand, it is known that precise control of the temperature of a resistively-heated heating element can be achieved using a power supply that supplies direct current waveform.

It would therefore be desirable to provide a power supply that provides the safety features inherent in using a high frequency alternating-current signal, but with the temperature control achievable with a direct current power supply.

Tamura U.S. Pat. No. 4,549,073 describes a DC power supply for use with resistively-heated heating elements. The power supply described in that patent employs a fixed DC sense current to derive a heating element resistance. While the device described in that patent provides temperature regulation of the heating element, supply of the DC drive current to provide power to the heating element must be interrupted during the resistance measuring operation. Thus, the heating element temperature cannot be measured during the heating process. Further, the circuitry used to switch between the DC power signal and the DC sense circuit adds complexity and additional cost to the design of the supply. Additionally, as discussed above, the power supply uses undesirable DC power to generate heat in the heating element.

It would therefore be desirable to be able to provide a power supply that allows the heating element temperature to be monitored while simultaneously powering the heater yet does not employ DC power to heat the heating element.

Tamura et al. U.S. Pat. No. 4,523,084, Japanese Utility Model Publication No. 51-15160 and Japanese Utility Model Publication No. 51-110615, also describe power supplies for use with resistively-heated heating elements. However, those reference also employ undesirable DC power to heat the heating element.

SUMMARY OF THE INVENTION

In view of the foregoing, it is an object of the present invention to provide a power supply for hemostatic surgical instruments that enables the operator to select a desired instrument operating temperature on the power supply control panel, and that monitors instrument temperature and adjusts the power delivered to the instrument to maintain a substantially constant instrument operating temperature under varying thermal loads.

It is another object of the present invention to provide a power supply for resistively-heated heating elements that allows the heating element temperature to be monitored while simultaneously powering the heating element.

It is an object of the present invention to provide a power supply offering the safety features associated with high frequency alternating-current power supplies and the temperature control precision obtainable with direct current power supplies.

These and other objects of the invention are accomplished in accordance with the principles of the present invention by providing a power supply that has circuitry to drive resistively-heated surgical instruments. The power supply of the present invention advantageously utilizes the temperature-dependent character of the resistance of such heating elements, wherein the resistance of the heating element varies as a function of temperature. By measuring the instantaneous resistance of the heating element, the temperature of the instrument may be monitored.

The power supply of the present invention provides circuitry for receiving a setpoint resistance signal indicative of a selected instrument operating temperature from a processor and comparing it to the measured resistance signal of the heating element to generate a control signal. Circuitry is also provided that generates an appropriate level of AC power for heating the instrument in response to the control signal, so that the instrument is maintained at the selected temperature, substantially independent of the applied thermal load.

The power supply of the present invention offers improved precision in controlling the temperature of the resistively-heated surgical instrument by supplying a direct current sense signal in the form of a current or voltage signal to the heating element in order to continuously monitor the temperature of the heating element, while simultaneously supplying AC power to heat the heating element. The resulting DC voltage drop or DC current in response to the direct current sense signal is then measured to provide a feedback signal that is indicative of the instantaneous heating element temperature, which in turn is compared to the set-point signal to generate the power level control signal.

BRIEF DESCRIPTION OF THE DRAWINGS

The above and other objects and advantages of the invention will be apparent upon consideration of the following detailed description, taken in conjunction with the accompanying drawings, in which like reference numerals refer to like parts throughout, and in which.

DETAILED DESCRIPTION OF THE INVENTION

Figure 1:
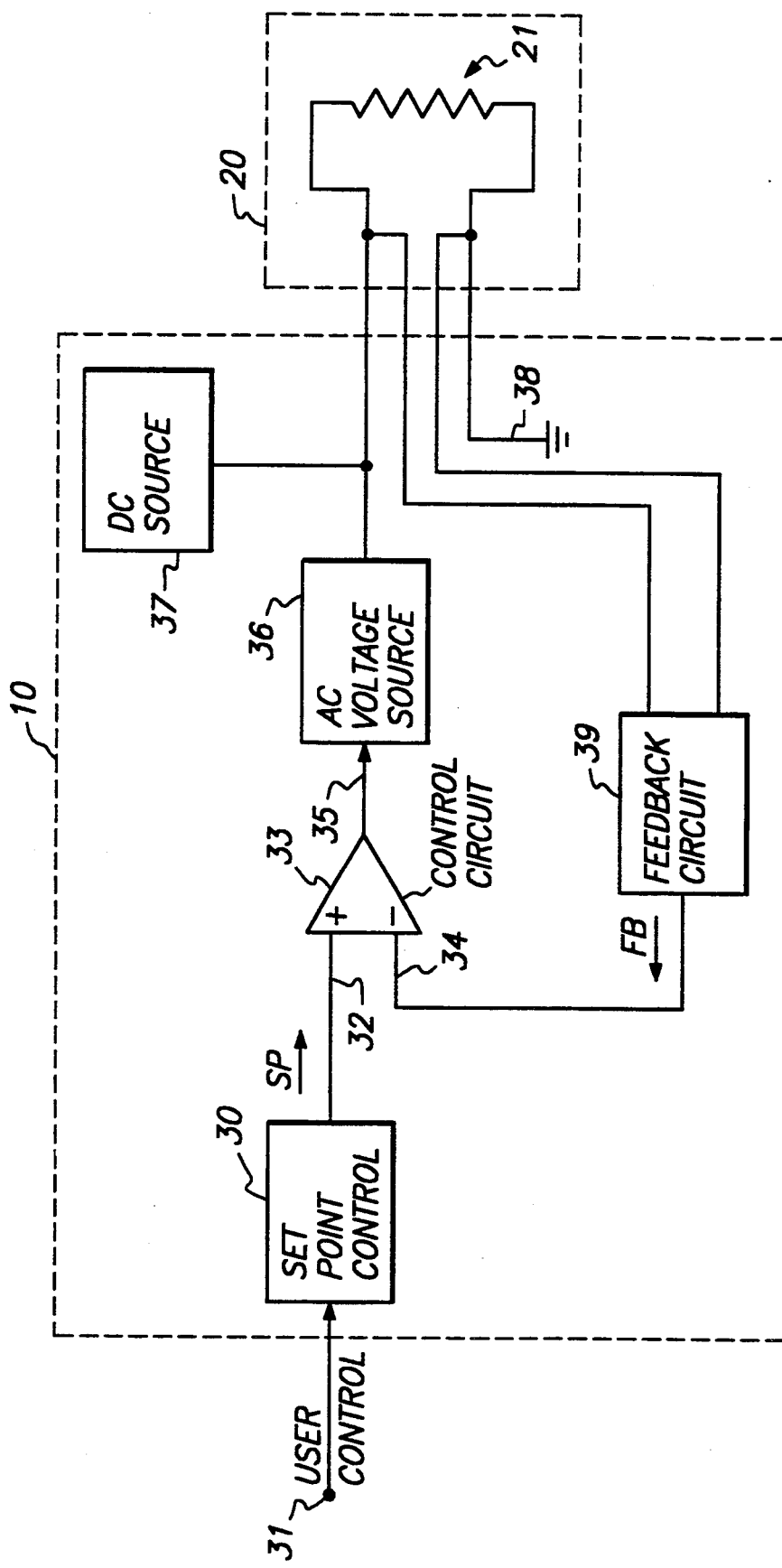
FIG. 1 is a schematic diagram of the power supply of the present invention, including an attached resistively-heated surgical instrument.

Referring to FIG. 1, an embodiment of power supply 10 in accordance with the principals of the present invention 13 is described. Depending on the desired operating temperature of surgical instrument 20, an operator selects a desired temperature set point. This temperature set point may be selected using a control knob, keyboard or other convenient user interface (not shown) associated with power supply 10. The selected set point signal is received by set point control 30 via input terminal 31. Set point control 30 provides an appropriate set point control signal SP to control circuit input terminal 32 of control circuit 33.

Control circuit 33 compares the received set point control signal SP with a feedback signal FB received via control circuit input terminal 34. A control signal proportional to the difference between the set point control signal SP and the feedback signal FB is generated by control circuit 33 and provided to input terminal 35 of AC voltage source 36. AC voltage source 36 provides an AC voltage having a magnitude proportional to the control signal to heating element 21 of heated instrument 20, thereby producing a temperature rise by ohmic heating.

To maintain the selected temperature, the resistance of heating element 21 is monitored and fed back to control circuit 33. Heating element 21 has a resistance that varies as a function of temperature. If the temperature is too high or too low, the resulting resistance variation in heating element 21 is detected and the corresponding control signal is generated by control circuit 33 and received by AC voltage source 36.

The resistance of heating element 21 may be measured by providing a predetermined DC signal from DC source 37 across heating element 21 to ground terminal 38. A resulting DC resistance signal is detected by feedback circuit 39, which cancels the AC voltage from the DC resistance signal, and provides the feedback signal FB to control circuit 33.

It can thus be seen that the circuitry of power supply 10 shown in FIG. 1 provides control of the temperature of surgical instrument 20 in accordance with the desired temperature set point selected by the operator.

Figure 2:
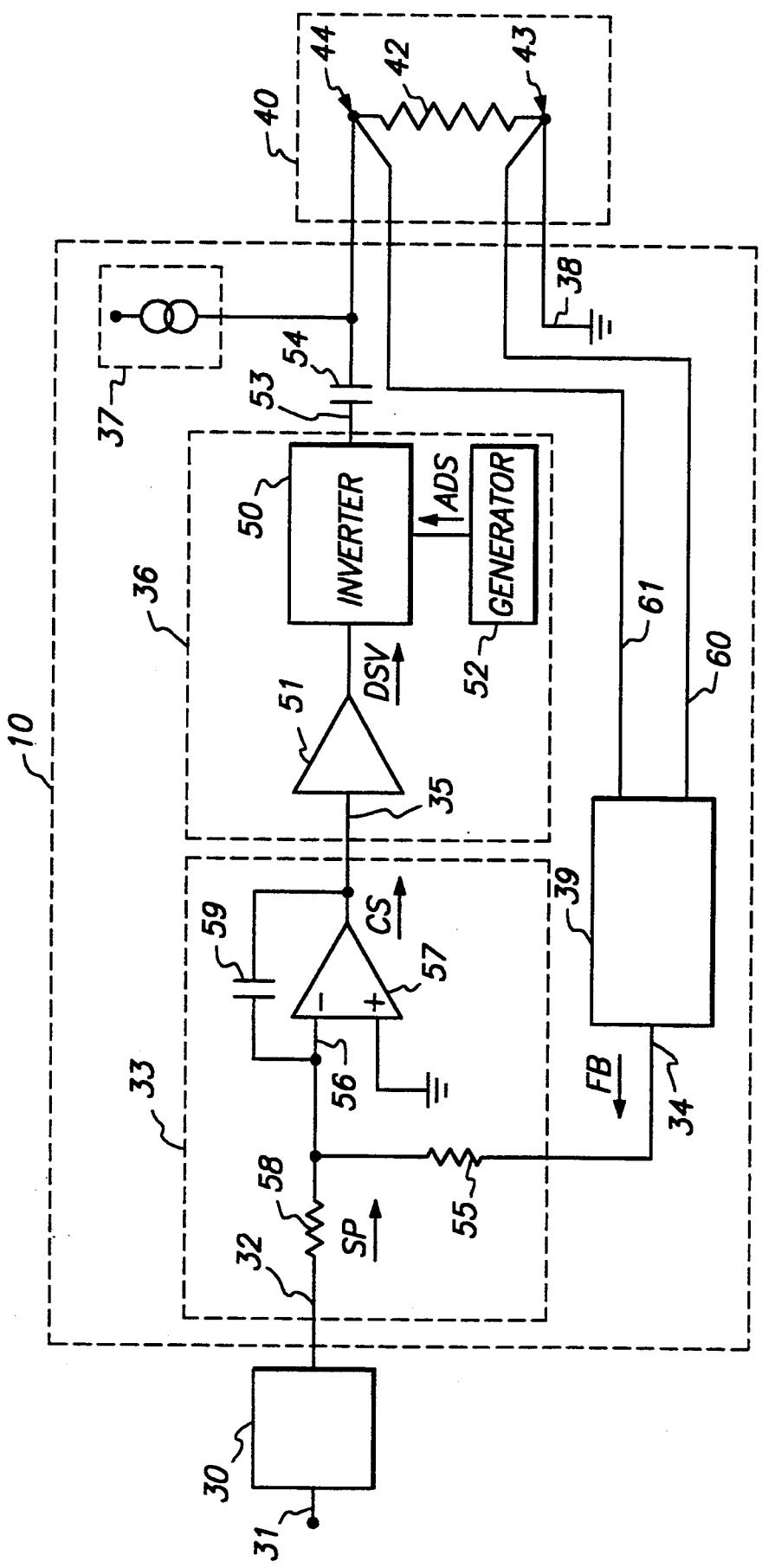
FIG. 2 is a circuit diagram of a preferred embodiment of the power supply of FIG. 1.

Referring now to FIG. 2, a preferred embodiment of a power supply constructed in accordance with the principles of the present invention is described. For purposes of illustration, power supply 10 has resistively-heated surgical scalpel 40 attached. Scalpel 40 can be any type of resistively-heated scalpel, however, preferably, it is of a type described in concurrently-filed, commonly-assigned, copending U.S. patent application Ser. No. 07/877,698, which has two heating elements, one at the tip of blade, and another at the heel of the blade. Power supply 10 therefore may include circuitry for driving both the tip and the heel heating elements of scalpel 40. For clarity, only the circuitry for operating the heel heating element 42 of scalpel 40 is described herein. It is to be understood, of course, that the circuitry for powering the tip heating element of scalpel 40 operates in a similar identical manner. In general, a hemostatic surgical instrument may have any number of heating elements, having resistances that range from 5 to 20 ohms and drawing power in the range of 50 to 150 watts.

Resistive heating element 42 of scalpel 40 is in thermal communication with the cutting edge of the blade (not shown), so that the heat generated in heating element 42 is conducted to the cutting edge of the blade. Direct current and low frequency currents are known to cause adverse neuromuscular stimulation in the patient as described above. Accordingly, as described in the aforementioned U.S. patent application Ser. No. 07/877,698, resistive heating element 42 includes an electrically-insulating coating.

The power supply of the present invention provides additional safety against the potential of current leakage, for example through a pinhole in the electrically insulating coating, by supplying power to the resistive heating element in the form of a high frequency alternating-current (AC) waveform. The frequency of this AC waveform is preferably above 100 kHz, to reduce the likelihood of undesirable neuromuscular stimulation.

Power supply 10 of the present invention provides an AC voltage output to the resistively-heated surgical instrument, and varies the instantaneous power supplied to heating element 42 of the surgical instrument in order to maintain the heating element at a pre-determined resistance, and thus, temperature. The AC voltage source 36 of power supply 10 includes inverter 50 that accepts a DC supply voltage DSV from modulator 51, transforms the supplied voltage into a high voltage, and gates the transformed voltage to heating element 42 of the surgical instrument using a fixed-voltage AC drive signal ADS from generator 52.

Modulator 51, which is described in concurrently filed, commonly assigned, copending U.S. patent application Ser. No. 07/877,533, and hereby incorporated by reference, accepts a control signal CS via input terminal 35. The value of the control signal CS determines the magnitude of the DC supply voltage DSV provided to inverter 50, which, in turn, determines the peak-to-peak voltage of the AC power that is supplied to resistive heating element 42 via power output 53. Generator 52, modulator 51, and inverter 50 therefore form an AC voltage source having an adjustable AC output that has a waveform proportional to that of the fixed-voltage AC drive signal ADS and a peak-to-peak voltage level proportional to that of the DC supply voltage DSV.

Resistive heating element 42 has a resistance that varies as a function of temperature as described heretofore. Conduction of an AC current in resistive heating element 42 causes I²R heating. This heating of heating element 42 results in an increase in the temperature of heating element 42, which in turn causes the electrical resistance of the heating element to rise.

DC source 37, preferably a current supply providing a fixed DC current through resistive heating element 42, creates a DC voltage signal that is used to measure, through feedback circuit 39, the resistance of heating element 42. The DC current from DC source 37 flows through resistive heating element 42 to ground terminal 38, but is isolated from inverter 50 by blocking capacitor 54. As discussed above, although the present embodiment employs a DC current source to monitor the resistance of the heating element, a DC voltage source could as well be used in the alternative.

Figure 3:
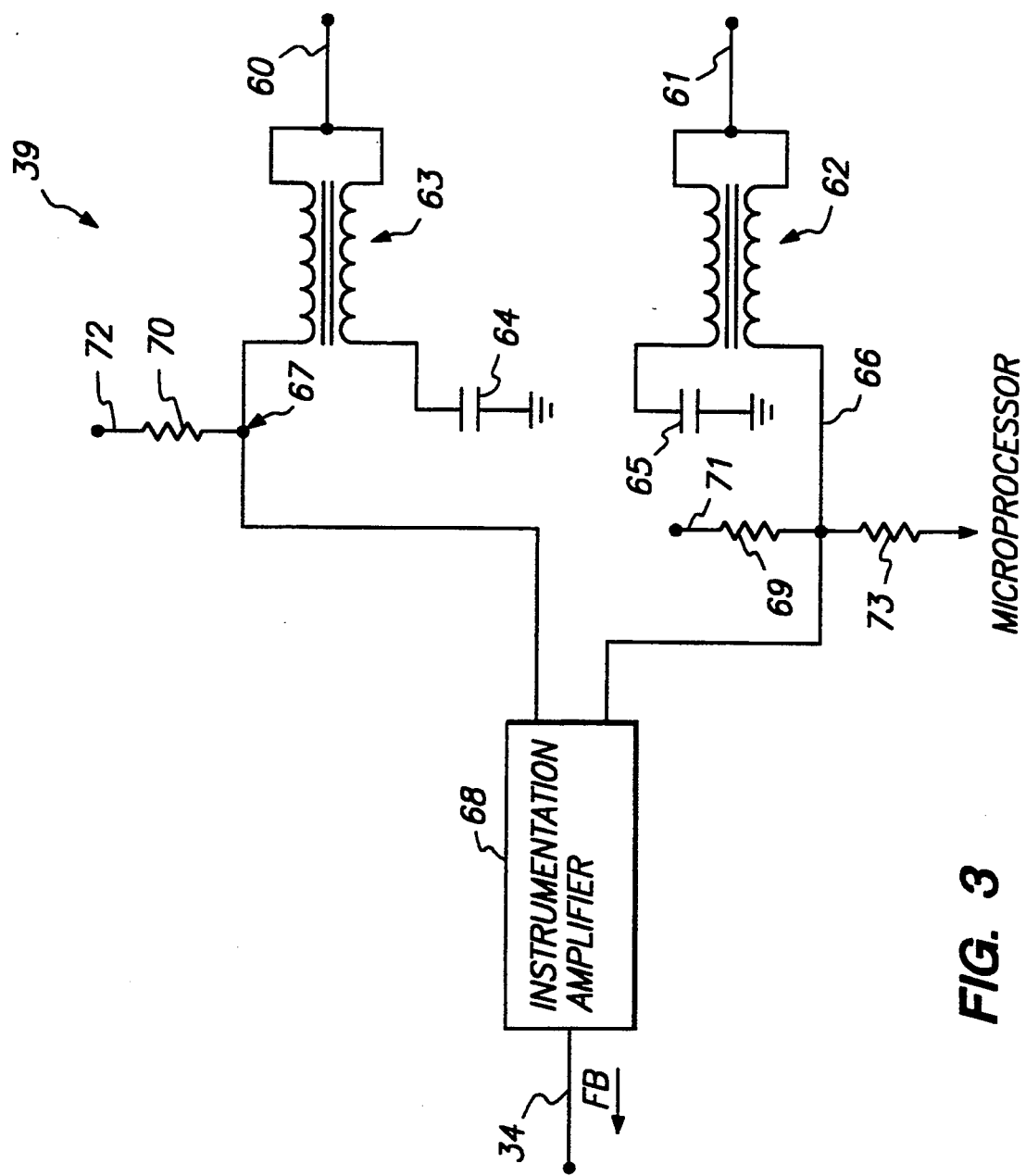
FIG. 3 is a circuit diagram of a preferred feedback circuit according to the present invention.

A preferred embodiment of feedback circuit 39 is shown in FIG. 3. Feedback circuit 39 serves to accurately extract the DC feedback signal from across resistive heating element 42. Feedback terminal 60 receives the nominally grounded signal from terminal 43 adjacent one side of heating element 42 of scalpel 40, while feedback terminal 61 is connected to terminal 44 adjacent the other side of heating element 42. Transformers 62 and 63 cancel the AC signal component present at terminals 61 and 60, respectively. Capacitors 65 and 64 present a low impedance path to ground, which allows the mutuality of the primary and secondary windings of transformers 62 and 63 to cause a magnetic cancellation of the input, providing filtered DC signals at terminals 66 and 67, respectively. The difference between the signals at terminals 66 and 67 is measured by instrumentation amplifier 68, which produces at terminal 34 the feedback signal FB that is proportional to that difference.

Resistors 69 and 70 prevent the output of power supply 10 from being driven high in the event that scalpel 40 is accidentally disconnected from the circuit. Were the scalpel to be disconnected, shutdown node 71 would pull node 66 high, and shutdown node 72 would pull node 67 low, shutting down power supply 10.

If desired, a signal proportional to the DC voltage across resistive heating element 42 may be provided via resistor 73 for use with a microprocessor-based controller (not shown).

Referring back to FIG. 2, the DC voltage signal from feedback circuit 39 is passed via scaling resistor 55 to error amplifier inverting (−) terminal 56 of error amplifier 57 (the non-inverting (+) terminal of which is coupled to ground). A resistance setpoint voltage of opposite polarity corresponding to the desired operating temperature of the instrument is also provided at error amplifier inverting (−) terminal 56 by set point control 30 via scaling resistor 58. The DC voltage signal and the resistance setpoint voltage are compared by forming a sum at error amplifier inverting (−) terminal 56. Error amplifier 56 and integrating capacitor 59, which supplies a dominant pole, provide a control signal proportional to that sum, which is input to modulator 51, thus completing a feedback loop. If the DC voltage signal has, proportionally, a relatively larger magnitude than the resistance setpoint voltage, the DC voltage supplied by modulator 51 decreases, as does the AC power supplied by inverter 50. This allows the temperature of the instrument to fall toward the selected operating temperature. If, however, the DC voltage signal has, proportionally, a relatively smaller magnitude than the resistance setpoint voltage, the AC power increases, causing the temperature of the heating element to rise. The circuitry of the present invention therefore regulates the temperature of a resistively-heated surgical instrument about the selected temperature.

In a preferred embodiment of the present invention, power supply 10 provides a AC voltage waveform of 0–45 volts peak-to-peak to heating element 42 at a frequency of 400 kHz. Such a power supply is able to heat a heating element having a resistance that varies from 6–8 ohms at room temperature to approximately 12–16 ohms at typical operating temperature of about 300° C.

Transformers 63 and 62 of feedback circuit 39 preferably have inductances of approximately 1325 μH and may have single toroidal cores such as Ferroxcube 768XT188-3C8 or 3C81 type, available from Ferroxcube of Riviera Beach, Fla. and have 30 turns of bifilar #30 wire. Shutdown node 71 is preferably held at 12 V and shutdown node 72 is held at −12 V. Resistors 69, 70 and 73 have respective resistances of 3 KΩ, 3 KΩ and 1 KΩ. Capacitors 64 and 65 have capacitances of 10 μF each. Instrumentation amplifier 68 may be formed from a 4×1 KΩ resistor network and an operational amplifier. Set point control 30 is preferably microprocessor-based.

Current supply 37 provides a regulated 100 mA current. Blocking capacitor 54 has a 1 μF capacitance and scaling resistors 58 and 55 have resistances of 3 KΩ and 1 KΩ, respectively. Capacitor 59 has a capacitance of 0.1 μF.

One skilled in the art will appreciate that the present invention can be practiced by other than the described embodiments, which are provided for purposes of illustration and not of limitation, and the present invention is limited only by the claims that follow.

What is claimed is:

1. A power supply for supplying AC power to a surgical instrument having a resistively-heated heating element, the heating element having a resistance that varies with temperature, the power supply comprising:

an AC voltage source for providing an AC voltage to the heating element, the AC voltage having a waveform with a cyclically varying instantaneous amplitude, the AC voltage responsive to a control signal and sufficient to heat the heating element to an operating temperature;

a DC source for simultaneously providing a predetermined DC signal to the heating element so that the AC voltage and predetermined DC signal produce a composite signal having both an AC voltage component and a DC signal component;

a feedback circuit adapted for receiving the composite signal from a location adjacent the heating element within the surgical instrument, the feedback circuit having means for filtering the DC signal component from the composite signal, independently of the instantaneous amplitude of the AC voltage, to provide a DC resistance signal, the feedback circuit providing a feedback signal indicative of the instantaneous resistance of the heating element in response to the DC resistance signal;

a set point control for providing a set point control signal indicative of a desired operating temperature; and a control circuit for providing the control signal in response to the feedback signal and the set point control signal, wherein the AC voltage source supplies an AC voltage to maintain the heating element substantially at the desired operating temperature.

2. The power supply of claim 1 wherein the AC voltage source comprises:
- a modulator for receiving the control signal and for providing a DC supply voltage proportional to the control signal;
- generator means for providing an AC drive signal; and
- an inverter coupled to the modulator, the generator means, and a power output for providing the AC voltage to the power output, the AC voltage having a waveform proportional to the AC drive signal and a peak-to-peak voltage proportional to the DC supply voltage.

3. The power supply of claim 2 wherein the control circuit comprises:
- an amplifier;
- a first resistor connected between the set point control and the amplifier for providing the set point control signal from the set point control to the amplifier; and
- a second resistor connected between the feedback circuit and the amplifier for providing the feedback signal to the amplifier, the amplifier providing the control signal to the modulator, the control signal being proportional to a sum of the set point control signal and the feedback signal.

4. The power supply of claim 1 wherein the DC source is a DC current source and the DC resistance signal is proportional to the instantaneous resistance of the heating element.

5. The power supply of claim 1 wherein the feedback circuit comprises:
- first and second feedback input terminals, the first and second feedback input terminals receiving the composite signal;
- an instrumentation amplifier for providing the feedback signal, the feedback signal being proportional to the DC resistance signal;
- and the means for filtering comprises
- a first transformer connected to the first feedback input terminal and
- a second transformer connected to the second feedback input terminal, the first and second transformers cancelling the AC voltage component to produce the DC resistance signal.

6. The power supply of claim 1 further comprising blocking means coupled between the AC voltage source and the heating element for isolating the AC voltage source from the DC source.

7. The power supply of claim 5 wherein the blocking means is a blocking capacitor.

8. A power supply for supplying AC power to a surgical instrument having a resistively-heated heating element, the heating element having a resistance that varies with temperature, the power supply comprising:
- a current supply for supplying a DC sense current to the heating element, the sense current generating a DC voltage signal proportional to the resistance of the heating element;
- an AC voltage supply for receiving a control signal and providing the AC power proportional to the control signal, the AC power provided simultaneously with the DC sense current and having a waveform with a cyclically varying instantaneous amplitude, the AC voltage supply having:
  - an input terminal for receiving the control signal, and
  - a power output for supplying the AC power to the heating element;
- a blocking capacitor coupled between the power output and the heating element for isolating the AC voltage supply from the DC voltage signal;
- a feedback circuit coupled to the heating element and adapted for receiving a composite signal comprising the AC power and the DC voltage signal, the feedback circuit including means for filtering the composite signal to cancel the AC power from the composite signal, independently of the instantaneous amplitude of the AC power, to provide a feedback signal indicative of the instantaneous resistance of the heating element;
- an error amplifier coupled to the input terminal for providing the AC voltage supply with the control signal, the error amplifier having an error amplifier input;
- a first resistor coupled between the feedback circuit and the error amplifier input for passing the feedback signal from the feedback circuit to the error amplifier; and
- a second resistor coupled to the error amplifier input for passing a resistance setpoint voltage to the error amplifier, the control signal provided to the AC voltage supply having a magnitude proportional to a sum of the resistance setpoint voltage and the feedback signal.

9. The power supply of claim 8 wherein the AC voltage supply comprises:
- a modulator coupled to the input terminal for receiving the control signal and for providing a DC supply voltage proportional to the control signal;
- generator means for providing an AC drive signal; and
- an inverter coupled to the modulator, the generator, and the power output for providing the AC power to the power output, the AC power having a waveform proportional to the AC drive signal and a peak-to-peak voltage proportional to the DC supply voltage.

10. The power supply of claim 9 further comprising:
- a capacitor coupled between the error amplifier input and the input terminal for supplying a dominant pole.

11. The power supply of claim 10 further comprising processor means coupled to the second resistor for providing the resistance setpoint voltage to the error amplifier input.

12. The power supply of claim 9 wherein the feedback circuit comprises:
- first and second feedback input terminals, the first and second feedback input terminals receiving the composite signal;
- and the means for filtering comprises
- a first transformer connected to the first feedback input terminal; and
- a second transformer connected to the second feedback input terminal, the first and second transformers cancelling the AC power from the composite signal to produce the feedback signal.

13. A method of supplying AC power to a surgical instrument having a resistively-heated heating element, for maintaining the heating element substantially at a desired operating temperature, the method comprising the steps of:
- applying AC power to the heating element from an AC voltage source, the AC power sufficient to heat the heating element to an operating temperature, the AC power having a waveform with a cyclically Varying instantaneous amplitude;

applying a DC sense signal simultaneously to the heating element to produce a composite signal having an AC power component and a DC signal component;

filtering the DC signal component from the AC power component independently of the instantaneous amplitude of the AC power component to produce a DC resistance signal indicative of the instantaneous resistance of the heating element.;

comparing the DC resistance signal to a resistance setpoint signal, the resistance setpoint signal indicative of the desired operating temperature; and varying the AC power in response to the comparison of signals, wherein the AC source supplies an AC voltage to maintain the heating element substantially at the desired operating temperature.

14. The method of claim 13 wherein the DC sense signal is a DC sense current, the DC resistance signal is a DC resistance voltage, and the resistance setpoint signal is a resistance setpoint voltage.

15. The method of claim 14 wherein the step of comparing comprises the steps of:
forming a sum of the DC resistance voltage and the resistance setpoint voltage; and
providing a control signal to the AC voltage source proportional to the sum.

16. The method of claim 15 wherein the step of varying the AC power comprises the steps of:
receiving the control signal; and
producing an increased AC power in response to the control signal.

17. The method of claim 16 wherein the step of producing an increased AC power comprises the steps of:
producing an increased DC supply voltage proportional to the control signal;
generating a fixed-voltage AC drive signal; and
supplying an AC output that has a waveform proportional to the fixed-voltage AC drive signal and a peak-to-peak voltage level that is proportional to the DC supply voltage.

18. The method of claim 15 wherein the step of varying the AC power comprises the steps of:
receiving the control signal; and
producing a decreased AC power in response to the control signal.

19. The method of claim 18 wherein the step of producing a decreased AC power comprises the steps of:
producing a decreased DC supply voltage proportional to the control signal;
generating a fixed-voltage AC drive signal; and
supplying an AC output that has a waveform proportional to the fixed voltage AC drive signal and a peak-to-peak voltage level that is proportional to the DC supply voltage.

* * * * *